United States Patent [19]

Cullick et al.

[11] Patent Number: 4,530,234

[45] Date of Patent: Jul. 23, 1985

[54] METHOD AND SYSTEM FOR MEASURING PROPERTIES OF FLUIDS

[75] Inventors: Alvin S. Cullick; Bert J. Warner, both of Dallas, Tex.

[73] Assignee: Mobil Oil Corporation, New York, N.Y.

[21] Appl. No.: 509,759

[22] Filed: Jun. 30, 1983

[51] Int. Cl.³ .................................................. G01N 11/00
[52] U.S. Cl. ............................................ 73/53; 73/54; 73/64.4
[58] Field of Search .................. 73/54, 53, 55, 64.4, 73/32 R

[56] References Cited

U.S. PATENT DOCUMENTS

| | | | |
|---|---|---|---|
| 2,957,338 | 10/1960 | Kennedy et al. | 73/54 |
| 4,224,821 | 9/1980 | Taylor et al. | 73/32 R |
| 4,258,564 | 3/1981 | Hulme et al. | 73/61 R |

FOREIGN PATENT DOCUMENTS 1549443 10/1967 France .................................. 73/54

Primary Examiner—Anthony V. Ciarlante
Assistant Examiner—Hezron Williams
Attorney, Agent, or Firm—Alexander J. McKillop; Michael G. Gilman; Charles J. Speciale

[57] ABSTRACT

Method and system for measuring properties of fluids, particularly of reservoir fluids involved in enhanced oil recovery, comprising a pair of high pressure cells, each one of the cells having a floating piston therein which separates the respective cell into a fluid analysis chamber and a hydraulic fluid chamber. Means are provided for selectively controlling the amount of pressure applied to the hydraulic fluid chamber of each cell, whereby the pressure of the fluid under analysis is defined. Means are also provided for interconnecting the fluid analysis chambers of each cell whereby fluid under analysis may be selectively passed between the cells.

16 Claims, 6 Drawing Figures

METHOD AND SYSTEM FOR MEASURING PROPERTIES OF FLUIDS

BACKGROUND OF THE INVENTION

1. Field of the Invention

The present invention relates to measuring properties of fluids. The invention is particularly suited for measuring properties of reservoir fluids involved in enhanced oil recovery. Such properties being, by way of example, phase equilibria, phase volumes, compositions, densities, viscosities, and interfacial tensions of fluids.

2. Description of the Prior Art

Multicomponent, multicontact phase behavior data on reservoir fluids are necessary for complete modeling of multicontact phase behavior which occur in miscible displacement processes. The typical experiment in the past has involved mixing of components in a single equilibrium cell. The contents are mixed by shaking or stirring and allowed to equilibrate by diffusion and convection. Samples of lower and upper phases are removed from the cell through taps, and their compositions are analyzed. For multicomponent systems in windowed cells, phase volumes are measured visually and compositions can be measured by refractive index. Phase densities and viscosities must be measured in separate experiments.

Franklin M. Orr and Matthew K. Silva, "Equilibrium Phase Compositions of $CO_2$-Hydrocarbon Mixtures: Measurement by a Continuous Multiple Contact Experiment," presented at the Third Joint SPE/DOE Symposium on Enhanced Oil Recovery, April 4–7, 1982, Tulsa, Okla., reports an apparatus for measuring phase equilibria, densities, viscosities, and interfacial tensions. Orr et al describes a continuous multicontact experiment (CMC) in which fluids are continuously injected, circulated and withdrawn. The CMC experiment can potentially produce data in a time short relative to the single contact cell. The major drawbacks of the CMC are that the system composition is never known exactly, there is no measurement of phase volumes, and relatively large samples must be removed for analysis and no more than two phases can be sampled.

Ralph Simon, "A Visual System for Measuring the Properties of Petroleum Reservoir Fluids," presented at the Annual AIChE Meeting, New Orleans, La., Nov. 8–12, 1981, reports an apparatus based on using a sapphire cell. The system is operable up to 20,000 psi and 400° F. All measurements except compositions are performed with the fluid remaining in the cell: density by gamma ray transmission, viscosity by torsional crystal vibration, interfacial tension by pendant drop and photon correlation spectroscopy, phase volumes by visual observation, and compositions by gas chromatography. A drawback in the design is that mercury is used as the pressure fluid; therefore, the system cannot be used for high carbon dioxide containing fluids because of mercury/$CO_2$ emulsion formation.

SUMMARY OF THE INVENTION

In accordance with the present invention, there is provided a method and system for measuring properties of fluids comprising a pair of high pressure cells, each one of the cells having a floating piston therein which separates the respective cell into a fluid analysis chamber and a hydraulic fluid chamber. Means are provided for selectively controlling the amount of pressure applied to the hydraulic fluid chamber of each cell, whereby the pressure of the fluid under analysis is defined. Means are also provided for interconnecting the fluid analysis chambers of each cell whereby fluid under analysis may be selectively passed between the cells.

In accordance with another aspect of the present invention, at least one of the cells has a bar magnet in its fluid analysis chamber, and means are provided externally of the cell for agitating the bar magnet.

The method and system of the present invention allows fluids to pass through physical property measurement instruments by using one cell as a receiver vessel. Further, no mercury comes into contact with fluid under analysis, and it is possible to sample as many fluid phases as are present.

DESCRIPTION OF SPECIFIC EMBODIMENTS

Figure 1:
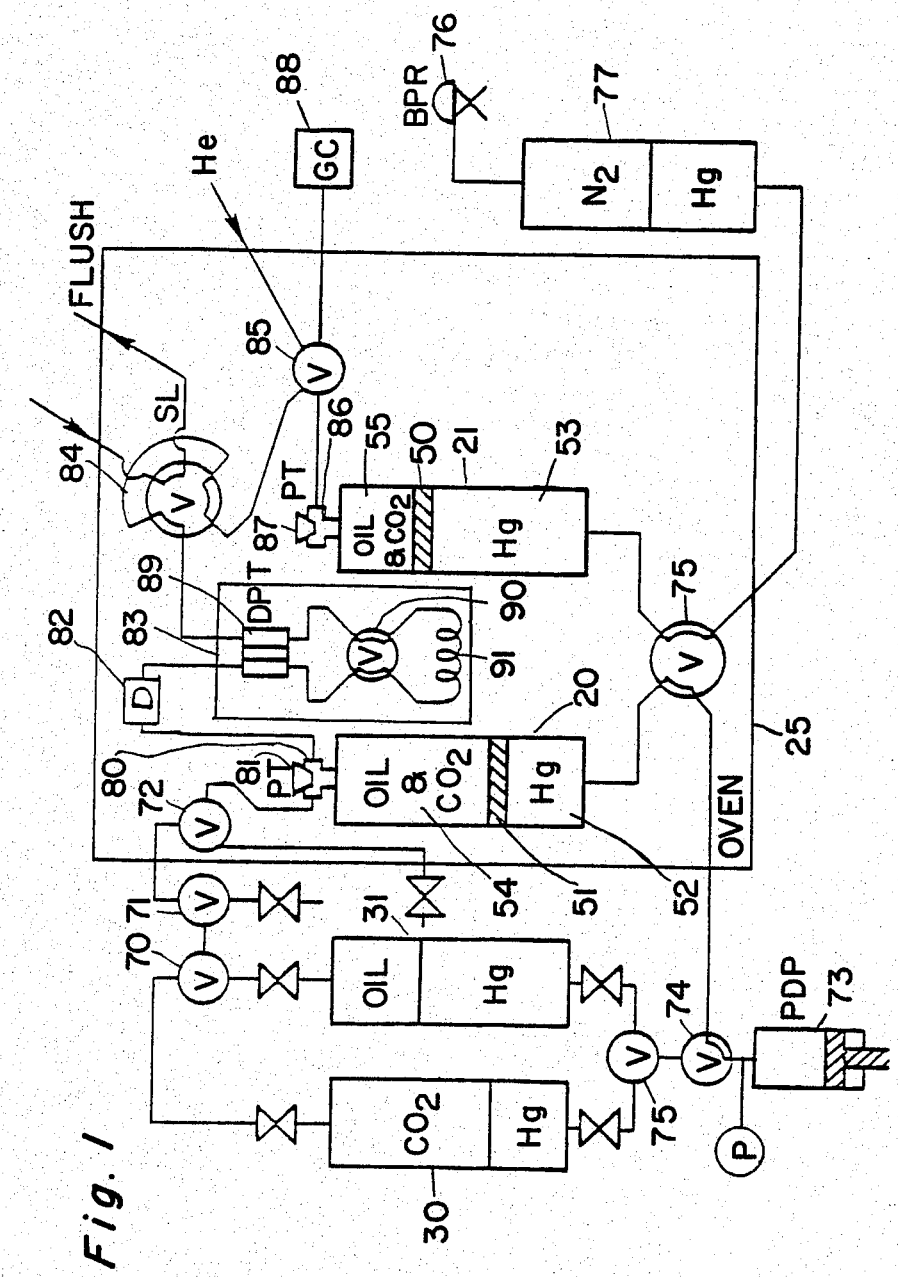
FIG. 1 is a schematic representation of a system for measuring properties of fluids in accordance with the present invention.

With Reference to FIG. 1, a pair of high pressure equilibrium cells 20, 21 are each provided with a floating piston 51, 50 which separates hydraulic pressure fluid, preferably mercury in a chamber 52, 53 from a fluid analysis chamber 54, 55. Specific mixture concentrations of fluid under analysis is fed to the high pressure equilibrium cells 20, 21 from supply vessels 30, 31 through a valve arrangement 70, 71, 72. A positive drive pump 73 provides hydraulic pressure on supply vessels 30, 31, through valves 74, 75. The positive displacement pump 73 also provides hydraulic pressure applied to the high pressure equilibrium cells 20, 21 through the valve 74 and a valve 75. Pressure is regulated on the hydraulic system thus far described by a back pressure regulator 76 with a vessel 77 having nitrogen as a pressure buffer to mercury used as the hydraulic fluid.

Fluid is fed to fluid analysis chamber 54 of the high pressure equilibrium cell 20 through an end closure and tee adapator 80, which has a pressure transducer 81 therein. Fluid exits the fluid analysis chamber 54 through the end closure and tee adaptor 80 to a densimeter 82. The densimeter 82 is connected to a viscometer 83. The viscometer 83, in turn, is connected by valves 84 and 85 with an end closure and tee adaptor 86 of the fluid analysis chamber 55 of the other high pressure equilibrium cell 21. This end closure and tee adaptor 86 also has a pressure transducer 87 therein. Valve 85 also interconnects the end closure and tee adaptor 86 with a gas chromatograph 88.

The viscometer apparatus 83 includes a differential pressure transducer 89, a switching valve 90, and a capillary tube 91. The pair of high pressure equilibrium cells 20, 21, densimeter 82, viscometer 83 and associated valves 72, 75, 84, 85, are housed in an oven 25 which will be discussed hereinafter.

The arrangement shown in FIG. 1 allows a fluid system in high pressure equilibrium cell 20 to reach equilibrium by use of a magnetic stirrer, which will be described hereinafter with reference to FIGS. 4 and 5. The fluid in cell 20 can then be pumped to cell 21. As each phase passes through the system, its density, volume, viscosity, and composition are measured in turn. Additional fluids may be metered into the system at any time or a specified volume of a phase can be flashed and flushed out of the system and flashed to atmospheric pressure for analysis.

Figure 4:
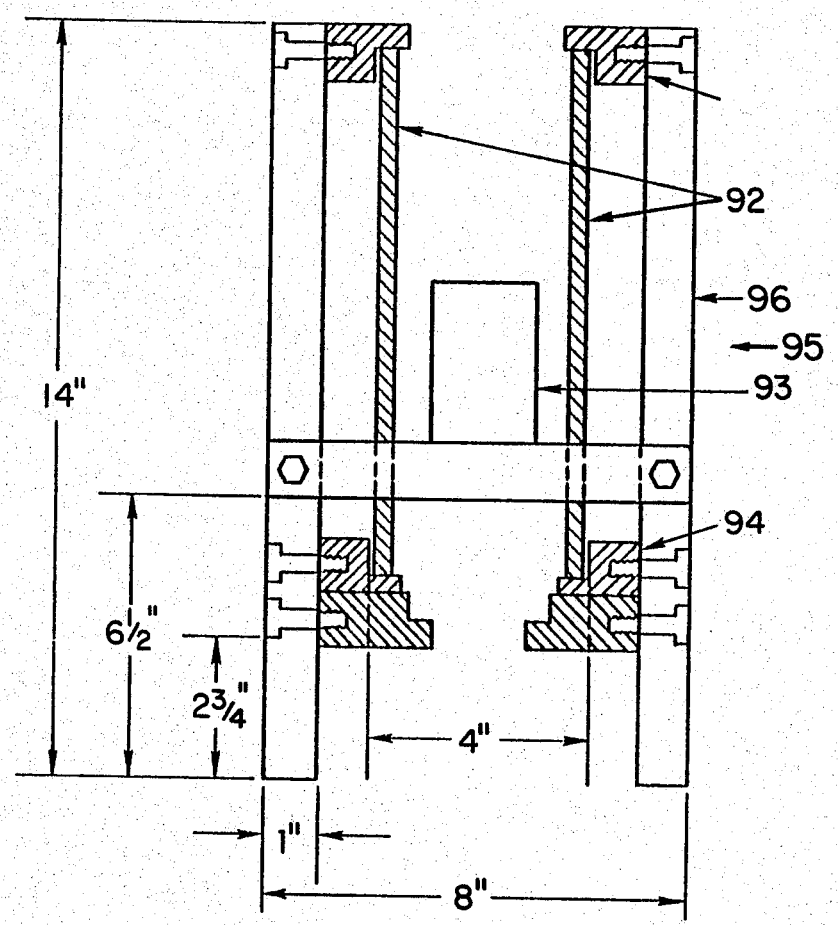
FIG. 4 is a cross-sectional schematic view of a magnetic stirrer for stirring one or both of the high pressure equilibrium cells.
Figure 5:
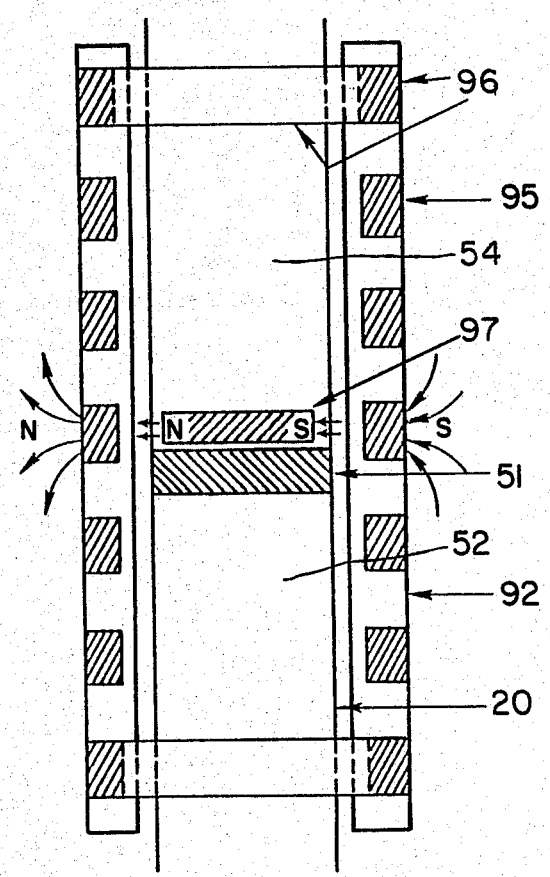
FIG. 5 is a suitable magnet configuration for the stirrer of FIG. 4.

Mixing to reach equilibrium can also be accomplished by switching the valve 90 to the position not shown such that capillary tube 91 is bypassed, and passing fluid back and forth between the cells 20, 21 while stirring fluid in cell 20 with the magnetic stirrer of FIGS. 4 and 5. The invention also contemplates that the cell 21 also include the magnetic stirrer of FIGS. 4 and 5.

The switching valves are preferably 3-, 4-, or 6-port Valco valves made of Nitronic 60 stainless steel and designed for continuous operation at 5000 psi at 150° C. The bore in each valve is 0.030 inches.

The regulator 76 can be a dome-type back pressure regulator. All connecting tubing can be ⅛ inch OD, 0.055 inch ID stainless steel. The approximate fluid volumes associated with system components can be as follows: for the high pressue cells 20, 21, 30, and 31,—200 cm$^3$; for the densimeter 82—1 cm$^3$; for differential transducer 89—4 cm$^3$; for viscometer 83—1.5 cm$^3$; and for the connecting tubing—1.5 cm$^3$. Thus, the system volume excluding the cells can be approximately 8 cm$^3$.

High Pressure Cells

Figure 2:
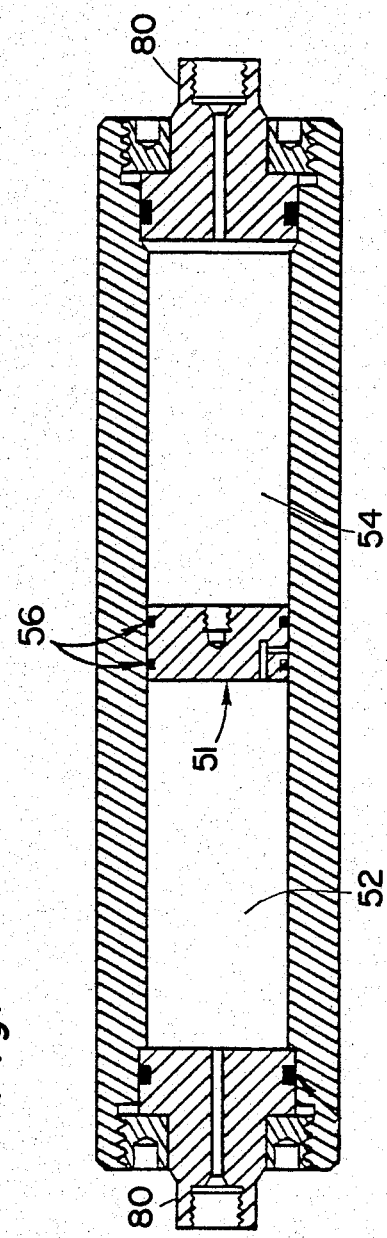
FIG. 2 is a cross-sectional view of one of the two high pressure equilibrium cells used in the embodiment of FIG. 1.

An embodiment of the high pressure cell 20, 21 is shown in FIG. 2. The cell 20, 21 may be constructed of 316 stainless steel and may be approximately 2.5 inches outside diameter and 1.5 inches inside diameter. The cell 20, 21 may be approximately 11 inches long or approximately 14 inches long. The cell 20, 21 suitably is designed for a maximum working pressure of 6000 psi at 280° F. Each cell has a piston 51 which may be constructed of Nitronic 60 stainless steel. The piston 51 is employed in each cell 20, 21 for separating mercury pressure fluid in one chamber 52 from the hydrocarbon fluids in the other chamber 54. The volume in each 11 inch cell is approximately 200 cm$^3$ and in each 15 inch cell is approximately 330 cm$^3$.

The piston 51 must seal properly at a high pressure drop across it, yet move smoothly with less than one psi pressure drop across it. This has been achieved by using double O-rings 56. O-rings which are in contact with mercury suitably are Viton 90, while those in contact with oil are Buna-N. Dense carbon dioxide swells rubber-based O-rings causing eventual O-ring failure. Swelling is most severe when there is a large amount of carbon dioxide in the system and the pressure is cycled from ambient to above 1000 psi and back to ambient. New O-rings should be inserted after several pressure cycles to ambient, whenever carbon dioxide has been in the system. Piston sticking, can be eliminated or at least minimized by having a piston length of 1.5 inches.

The cell 20, 21 has an end closure and a tee adapter 80 at each end thereof. The end closures and tee adapter 80 are designed to require a minimum volume of fluid outside the cell, and the tee adapter is further designed for insertion of a pressure transducer 81, 87, such as Sensotec A205, into the fluid stream so that there is no dead volume associated with pressure measurement.

Constant Temperature Bath

The oven 25 is used as constant temperature bath, and may be a 2800 watt National Appliance Company (NAPCO) convection oven. The NAPCO oven was modified to a forced air type by installation of a fan at the top of the oven. The oven had internal dimensions of 41¼ inch width, 17½ inch depth, and 24 inch height. The main heater was moved from the bottom of the oven to the top to improve heat transfer and increase available space, and an additional 500 watt heater was installed as a control heater. The main heater output is set by variac control. Temperature is controlled by cycling the 500 watt heater, which may be controlled by a thermistor controller such as that manufactured by Yellow Springs Instruments, Inc. as Model 71A.

Temperature stability and temperature gradients were measured by placing thermocouples at various locations in the oven. Temperatures were allowed to stabilize for one hour before temperatures were measured. In the first set of measurements the thermocouples were in air. Table 1 presents results of the temperature homogeneity tests. Maximum temperature difference between any two locations in the oven is 0.3° C. at a nominal temperature of 93° C. and 0.07° C. at nominal 37° C. In a second set of measurements, the thermocouples were inserted into oil-filled wells in steel blocks. Temperature remained stable to ±0.02° C. at 87° C. for several hours for each thermocouple location.

Temperature Measurement

Temperature measurement is accomplished with a set of twelve Type E thermocouples, nickel-chromium alloy versus copper-nickel alloy (chromel-constantan). A set of six of the thermocouples was calibrated against a standard platinum resistance thermometer as described hereinafter. The second set of six thermocouples was calibrated against one of the first set. The calibrations provide for an uncertainty in temperature measurements of less than ±0.03° C. (±0.06° F.).

Description of Thermocouples

Suitable thermocouples are manufactured by Omega Engineering. Each thermocouple has a Type E junction which is encased in a six foot, 0.04 inch diameter sheath of 304 stainless steel. Each is connected to reference junctions of chromel-copper and constantan-copper and are immersed in an Omega Engineering ice point reference cell, which maintains ice point conditions. The ice point cell has six individual thermocouple wells, each of which is filled with mineral oil. Each junction is connected by copper leads to an Omega Engineering six circuit thermocouple selector panel which has a six-contact selector switch that can be used to select one of the six thermocouples for readout of its thermal electromotive force (EMF) on a digital multimeter such as a Data Precision 3600 5½ digit multimeter.

Each thermocouple is always connected to the same reference junction and same jack on the selector panel, and each is immersed to the same depth in the ice point cell. Therefore, any EMF arising from the contacts or connections would be included in the thermocouple calibrations so that no correction needs to be added to measured EMFs. In order to test for the residual EMF due to contact connections, both the reference junctions and thermocouple junctions were immersed in the ice bath. For the four thermocouples tested, contact EMF averaged 1.6 microvolts, which is approximately equivalent to 0.03° C., which is the same as the uncertainty of the thermocouple measurements.

Calibration of Thermocouples

A set of six thermocouples, labelled 1 through 6, were calibrated against a platinum resistance thermometer. The platinum resistance thermometer (Leeds and Northrup, Ser. No. 1,639,557) was calibrated at the National Bureau of Standards and has constants of $a=0.003926514$, $\delta=1.496697$ ($t_{68}$), $R_o=25.5635$ in the equation $$t = R_t - R_o/aR_o + \delta(t/100-1)t/100,$$

where t is the temperature in degrees Celsius and $R_t$ is the measured resistance in ohms. The resistance across the resistance thermometer was measured using a Leeds and Northrup potentiometric Mueller bridge with mercury contacts and a Keithly null microvoltmeter. The thermocouples and the resistance thermometer were immersed to a depth of nine inches in a circulating bath consisting of thirty gallons of Dow Corning 710 fluid.

The resistance of the platinum thermometer and potential drop across each thermocouple was measured at eight temperatures between approximately 38° C. and 150° C. The EMF at each temperature was then compared with that for a Type E thermocouple reported in Robert L. Powell, William J. Hall, C. H. Hyink, and Larry L. Sparks, "Thermocouple Reference Table Based on IPTS-68," United States Institute of Basic Standards—U.S. National Bureau of Standards, 1974. The National Bureau of Standards (NBS) polynomial for Type E thermocouples is ninth order in temperature in degrees Celsius and is based on EMF measurements at 16 reference temperatures between 0° C. and 961° C., with five of the reference temperatures being between 0° C. and 150° C.

The NBS polynomial is reported to be uncertain by ±4.4 microvolts, which is about ±0.07° C. The difference between the measured EMFs and the NBS values ranged from 12 microvolts (about 0.2° C.) at 38° C. to 70 microvolts (about 1° C.) at 150° C. The differences between measured and NBS EMFs were fit to quadratic polynomial functions of the measured EMFs. The coefficients of these polynomials are listed in Table 2. The largest deviations between the measured and the correlated EMFs and their standard deviations are also listed in Table 2. The other set of six thermocouples were calibrated against thermocouple number 5, and their EMF data were treated in exactly the same way.

Using the correlations in Table 2, one can calculate the difference between a measured EMF and the NBS EMF. This difference is then added to the measured value, and the temperature is calculated using the NBS polynomial. In this study, the standard deviations from correlations of measured EMF range from 0.4 to 1.1 microvolts. With the exception of two thermocouples, the largest deviation was 2.1 microvolts. Thus, taking the uncertainty of a measurement to be 2 microvolts, the uncertainty in knowledge of the temperature may be taken to be ±0.03° C.

An interactive computer program, TCOUPLE, utilizes the correlations to convert an EMF measurement for any of the twelve thermocouples to temperature in Celsius upon input of the thermocouple number and measured EMF.

Pressure Measurement

Pressure is measured with strain gages such as Sensotec Type A205 foil strain gage transducers. Each transducer has a welded diaphragm which is flush with its end, so that there is no internal volume in the transducer. Each is temperature compensated to 250° F. over the 0–6000 psia full scale range, has a nominal linearity and hysteresis of 0.5 percent of full scale and has a nominal repeatability of 0.2 percent of full scale.

The transducer output signals are read on a transducer indicator, such as a Sensotec Model SA-10D which has a digital display of pressure with 1 psi resolution. The indicator had four input channels and a channel selector switch for digital readout of an individual transducer and was expandable to ten channels.

Each of four transducers were twice calibrated at a six month interval against a Chandler Engineering dead weight tester from 0–5000 psia. The results are summarized in Table 3. The hysteresis is defined as the absolute difference between a reading obtained upon increasing the pressure and that obtained upon decreasing the pressure to a desired pressure. The average of all values of hysteresis is 7 psi, or 0.1 percent of full scale (6000 psia). The repeatability is defined as the absolute difference between a first pressure measurement and one measured six months later at the same absolute pressure. The average of all repeatability differences is approximately 8 psi, or 0.14 percent of full scale. Both the hysteresis and repeatability are much better than the 0.5 percent of full scale specifications for the transducers.

Figure 3:
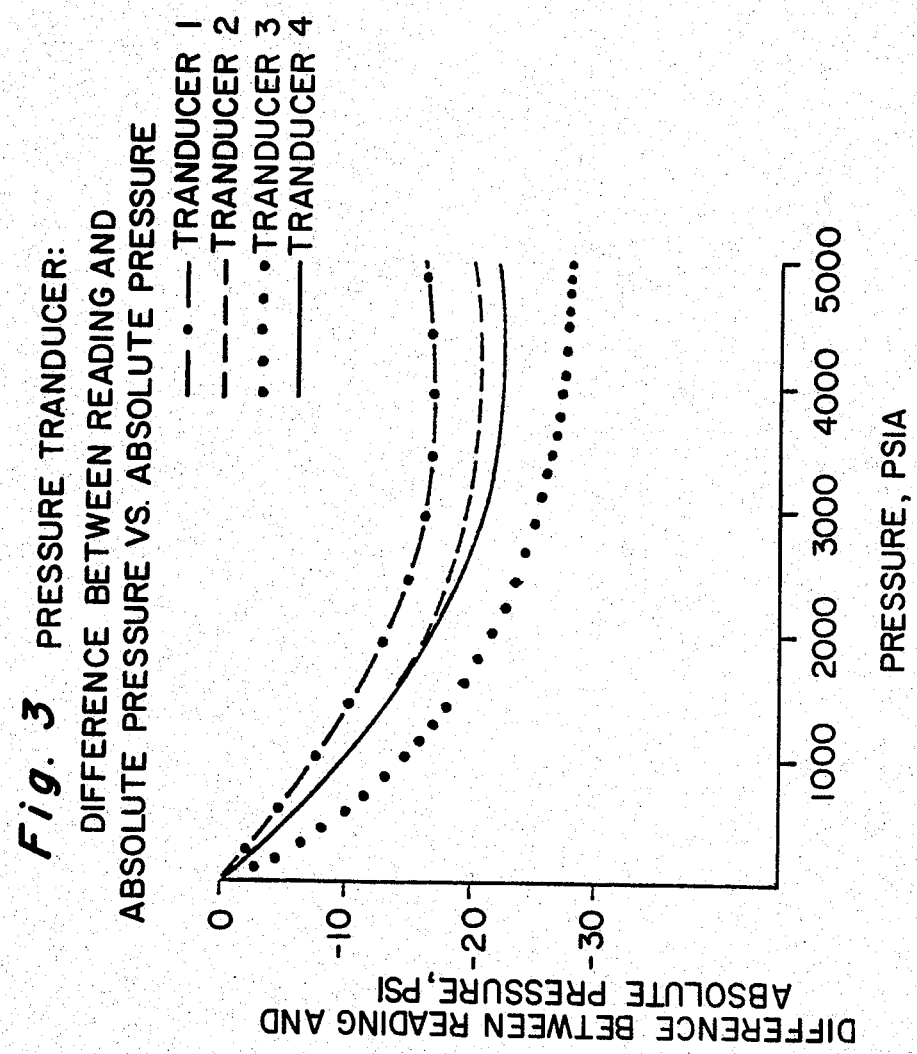
FIG. 3 is curves showing the difference between transucer pressure readings and absolute pressure versus absolute pressure.

The accuracy is the difference between the measured pressure and the true pressure. These differences are plotted in FIG. 3 for all four transducers using all the calibration data. Smoothed curves were drawn through the data to obtain a calibration correction curve for each transducer. Taking into account the hysteresis, repeatability, and calibration correction curves, pressure can be measured with an absolute accuracy of approximately ±10 psi.

The transducers are inserted into specially designed zero volume tee fittings as described hereinabove with reference to FIG. 2.

Density Measurement

Densities of fluids are measured using a high pressure densitometer cell 82, such as a Mettler/Paar DMA512 and frequency counter such as a Mettler/Paar DMA60 seven-digit frequency counter. The principal part of the DMA512 is a U-shaped stainless steel tube containing approximately one cubic centimeter of pore volume. The cell is fused into a double-walled cylinder through which a thermostatted fluid is circulated. There is a cavity surrounding the sample cell which is filled with a high thermal conductivity gas and which contains a capillary tube thermocouple well. The density determination is based on the principle of measuring the period of oscillation of the sample cell. The natural frequency of an oscillator is a function of the total mass of the oscillator. The density, p, of a sample in the cell is related to the period of oscillation of the cell containing the fluid by the following:

$$p = (1/A)(T^2 - B) \tag{1}$$

where A and B are cell constants which can be obtained from calibration measurements on samples of known density and T is the period of oscillation of the cell (reciprocal of oscillation frequency). When two different substances whose densities are known are measured, the following results:

$$p_1 - p_2 = k(T_1^2 - T_2^2) \tag{2}$$

where k is the instrument "k-factor" and is in general a function of temperature and pressure. The period of oscillation of the cell is read on the DMA60 electronic counter.

In order to measure densities of fluids to accuracies of ±0.1 percent or better, it is necessary to calibrate the DMA512 over the entire range of temperatures and pressures of interest for two substances with known densities that cover the range of expected sample densities. Thus, oscillation periods of water, carbon dioxide and nitrogen were measured from 500 to 5000 psia at every 500 psi for a total of nine pressures and 90° F. and 240° F. at every 30° F. for a total of six temperatures. The water was distilled and degassed prior to use. The nitrogen was nominal 99.995 percent pure and carbon dioxide was nominal purity 99.9999 percent. Pressures were measured using a type E thermocouple inserted in the DMA512 thermocouple well so that it was in thermal contact with the cell (see Temperature Measurement). An Exacal EX-100UHP constant temperature circulating bath circulated ethylene glycol through the cylinder containing the sample cell to maintain temperature to ±0.01° C. Two DMA512 cells were calibrated.

Instrument k-factors were obtained from the experimental results on water and nitrogen and the known densities of water and nitrogen by using Equation (2). These k-factors were then correlated as polynomial functions of temperature and pressure. Table 4 presents the k-factor correlations and Table 5 presents the average and largest deviations between experimental and correlated k-factors at each temperature. The largest deviation for both cells is 0.20 percent, and the average deviation for cell 1 is 0.05 percent while that for cell 2 is 0.08 percent. Table 6 presents the correlations and Table 5 presents values for the largest deviations between correlated and experimental periods of oscillation of water at each temperature. The largest deviation is 0.03 percent. The uncertainty in the k-factor correlation is the largest contribution to the uncertainty in a density computed from Equation (2), using measured temperature, pressure and oscillation period; therefore, the uncertainty in a density computed using the correlations is approximately ±0.1 percent for cell 2 and 0.05 percent for cell 1. The resolution on each instrument is approximately 0.0002 g/cm$^3$.

Although oscillation periods for carbon dioxide were measured over the entire temperature and pressure range, these data were not used in developing the k-factor correlations because oscillation periods and k-factors derived from carbon dioxide data could not be correlated within experimental error by a straightforward mathematical relation. This is due to the large sensitivity of carbon dioxide density to pressure and temperature in the range studied. However, the oscillation period data for carbon dioxide were used to calculate carbon dioxide densities from Equation (2) using the correlations in Tables 4 and 6. Table 7 presents a few results on carbon dioxide and compares carbon dioxide densities predicted by the International Union of Pure and Applied Chemistry (IUPAC) equation with those from Equation (2). (The IUPAC formulation is based on an analysis of all experimental carbon dioxide densities.) Of the twenty-one data presented, eleven measured densities are within the tolerance of the IUPAC density predictions. The average of the absolute differences between IUPAC and measured densities is 0.0014 g/cm$^3$ with a standard deviation of 0.0011 g/cm$^3$. Taking into consideration the additional effect of temperature and pressure uncertainties on the IUPAC carbon dioxide densities, which amount to ±0.001 g/cm$^3$ in the pressure range of 1000-3000 psi, the agreement is excellent.

The density of pure n-decane was measured at 30.3° C. in cell 30. Measured densities were 0.728 g/cm$^3$ and 0.733 g/cm$^3$ at 1000 and 2000 psia, respectively. Although there are no literature results at these same pressures and temperatures the results were compared with density predictions from the TRAPP program, described in Ely, J. F. and Hanley, H. J. M., "Prediction of Transport Properties, 1. Viscosity of Fluids and Mixtures," *Ind. and Chem. Eng. Fund.* 20, 323 (1981) which predicts 0.731 and 0.736±0.010 g/cm$^3$ at 1000 and 2000 psi, respectively, and with the COSTALD method, described in Hankinson, R. W. and Thomson, G. H., "A New Correlation for Saturated Densities of Liquids and Their Mixtures," *AIChE J.*, 25, 653 (1979) plus a pressure correction factor, which predicts 0.728 and 0.733±0.001 g/cm$^3$ at 1000 and 2000 psia, respectively, which is in perfect agreement with the measured values.

Viscosity Measurement

The capillary tube viscometer 83 suitably consists of a 287 inch long capillary tube 91 of approximately 0.014 inch diameter and a differential pressure transducer. In order to test the design and calibrate the system, pressure drops for pure carbon dioxide, toluene, n-decane, n-tridecane, and n-hexadecane were measured across a tube of the same diameter and at various constant flow rates, ranging from 2.34 cm$^3$/hr to 18.8 cm$^3$/hr. These flow conditions are expected to result in laminar flow for all fluids studied. Laminar flow was verified experimentally by demonstrating that the following relation holds:

$$\Delta P = c \cdot Q \tag{3}$$

where Q is volumetric flow rate, c is a constant and ΔP is the pressure drop across the capillary tube. The applicability of the Hagen-Pouiselle equation was also demonstrated, where the Hagen-Pouiselle equation is $$\Delta P = (8\eta l Q)/(\pi 1 a^4) \tag{4}$$

and a is the tube radius, 1 is the tube length and η is the fluid viscosity. The Reynold's numbers were always less than 0.03, and the end effects were calculated as less than 10-6 centipoise.

One of the above fluids was chosen as a calibration fluid with a known viscosity, from which a value of the effective tube radius could be calculated. Then, the viscosity calculated by Equation (2) using measured pressure drops was compared with literature values of viscosity found in J. F. Ely and H. J. M Hanley, "Prediction of Transport Properties, 1. Viscosity of Fluids and Mixtures", *Ind. and Chem. Eng. Fund.* 20, 323

(1981) and K. Stephan and K. Lucas, Viscosity of Dense Fluids, Plenum Press, 1979 for other fluids or the same fluid at different conditions. For example, the pressure drop for n-tridecane was measured at flow rates of 2.34 cm$^3$/hr to 6.2 cm$^3$/hr at 75° F. and 120° F. at 2200 psia. The effective diameter was calculated from the known viscosity at 75° F. and used to calculate a viscosity at 120° F. The measured viscosity at 120° F. agreed with literature viscosity exactly. In another case, the tube diameter was calculated by the pressure drop for n-hexadecane and the pressure drop to be expected for pure carbon dioxide at the same temperature and pressure was predicted within experimental error.

Sensotec wet/wet differential pressure transducers (0 to 5 psid or 0 to 50 psid) were used to measure pressure drops. Each has a 5000 psi line pressure rating and a 1500 psi overrange on one side. The 5 psid transducer is rated to 0.5 percent full scale accuracy or 0.025 psid, and the 50 psid transducer is rated to 0.5 percent full scale, or 0.25 psid, accuracy. The 50 psid transducer had approximately 4 cm$^3$ of fluid fill volume in a dead end configuration, so that the transducer contributed 4 cm$^3$ of fluid dead volume to the phase equilibrium system. The end plates and fittings were modified to a flow-through configuration with less than 0.9 cm$^3$ fill volume, thus eliminating all dead volume and reducing the fluid volume. The end plates for the 5 psid transducer were also modified. As received from Sensotec, the transducer had more than 7 cm$^3$ of fluid fill volume and the inlet and outlet ports were 90° with respect to each other. The ports were moved to a 180° configuration and the fill volume was reduced to less than 3.4 cm$^3$.

Transducer output is read on a digital indicator, such as a Sensotec Model 450D digital indicator or a Sensotec SA-10D multifunction digital indicator. Each indicator outputs a voltage signal which is recorded on an Omniscibe pen recorder.

Magnetic Stirrer

In order to achieve thermodynamic phase equilibrium in a reasonable time, some mechanism for mixing the system fluid must be present. A mixing system must be capable of mixing the equilibrium cell 20 contents thoroughly in a short time, be mechanically reliable, and require a minimum of fluid volume outside the equilibrium cell. Fluid mixing may be by (1) shaking the cell or cell assembly; (2) continuously circulating the fluid; and (3) using an internal stirrer such as a shaft driven impellar or a magnetic bar.

In order to shake the cell 20 vigorously enough to thoroughly mix a light upper phase and a heavy lower phase and considering possible mechanical strains on the mercury and fluid connections to the cell, the entire cell assembly needs to be shaken. However, this would require a massive mechanical motor driven shaker that could possible effect performance of other system components e.g. the densitometer which is vibration sensitive.

Continuous circulation of the fluid through a circulating pump is another possibility and has been reported in Franklin M. Orr and Matthew K. Silva, "Equilibrium Phase Compositions of CO$_2$-Hydrocarbon Mixtures: Measurement by a Continuous Multiple Contact Experiment", presented at Third Joint SPE/DOE Symposium on Enhanced Oil Recovery, April 4-7, 1982, Tulsa, Okla. The system reported which utilizes continuous circulation, has a large volume of fluid outside the cell, cannot utilize a capillary tube viscometer because of pump pulsations, and must continuously feed fluid into the system in order to drive the fluid to the sampling valves. With continous feed and withdrawal, the actual system composition at any time is not known accurately. Further, with a piston drive cell, continuous circulation would require sophisticated seal assemblies for the tubes which carry fluid into and out of the cell.

A magnetic stirrer does not have the above drawbacks. It does not require any fluid volume outside of the cell nor does it require any special seals. It can be relatively small and mechanically straightforward. A schematic drawing of the magnetic stirrer is shown in FIG. 4. The stirrer 95 consists primarily of an aluminum stand 96, which supports an aluminum cylinder 92 and a DC motor 93, such as a Globe Industries 24 volt variable speed DC motor, which drives the cylinder 92 at 0 to 600 revolutions per minute (rpm) through a chain and sprocket coupling for a bearing race 94. The equilibrium cell 20 is supported along the axis of the cylinder 92 in a vertical position and remains stationary. There are fourteen 0.625 inch diameter by 0.365 inch deep holes cut into the cylinder 92 which are arranged in two sets 180° apart, each set containing seven holes which are spaced along a vertical line. A disc magnet, such as an Alnico 8 sintered, disc magnet is inserted into each hole. A schematic of the magnet configuration is shown in FIG. 5. The disc magnets 95 are held in place by a steel band 96 pinned vertically on the outside of the cylinder 92. Three other steel bands are arranged so that they encircle every other pair of magnets in a horizontal plane. The steel bands act to direct the orientation of the magnetic flux lines, as well as hold the magnets in place. The magnetic flux lines in the cylinder are primarily horizontal. The field strength is somewhat stronger in the plane of a magnet pair as compared with the plane in between a magnet pair.

A number of different magnetic bars were tested in several fluids to determine their characteristics for stirring. The maximum rpm achievable by the stirrer bar depends on the size, weight and geometry of the stirrer bar, the strength and geometry of the magnetic field, and the magnitude of viscous drag caused by the fluid. In order to be effective, the weight and size of the bar 97 must be balanced with the strength of the magnetic field and the fluid density so that the bar rests horizontally on the cell piston 20 and rotates at the same rate as the cylinder 92 on the piston 51 in the fluid analysis chamber 54. It must have as small a diameter as possible in order to minimize the volume of fluid remaining in the cell when the piston is at its top-most position in the cell. A magnetic bar 97 composed of Alnico 5, 0.125 inch diameter by 1.4 inch length, and inserted into Teflon tubing was found to be effective. Two bars of Alnico 8, each 0.125 inch diameter and 0.6 inch length when inserted in Teflon tubing so that there is a 0.1 inch gap between the bars in the center of the Teflon tube, were also found to be effective. These were tested in water (1 centipoise [cp] viscosity), solvasol (1 cp), mineral oil (13 cp), a system of solvasol and water, a system of mineral oil and water, and a silicone oil (100 cp). With the exception of silicone oil, the bars rotated up to 600 rpm and created a good vortex in the fluid. For the oil-water mixtures, a well-mixed emulsion with small bubbles was formed upon stirring. However, the stirrer bars could not rotate faster than approximately 200 rpm in the silicone oil. At that rate there was no vortex. Therefore, for fluids with viscosities greater than approximately 15 cp, further testing of the stirrer will be necessary in order to determine if a stronger magnetic field is required. The most viscous fluids which are presently being considered for studies in the apparatus are stock tank oils which have viscosities less than 10 cp.

Gas Chromatograph

Figure 6:
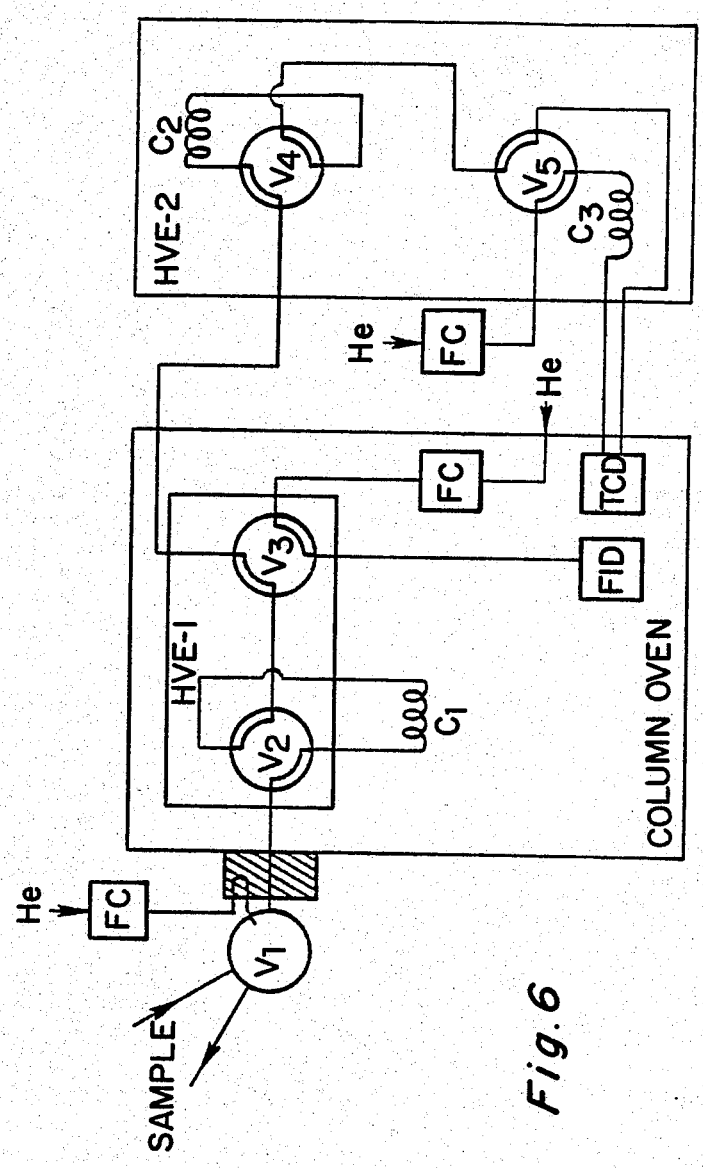
FIG. 6 is a schematic representation of a chromatograph valve system suitable for use in the embodiment of FIG. 1.

A gas chromatography system, such as Varian Instruments, Inc. Vista 64 gas chromatography system is suitable for phase composition measurements. The Vista 64 consists of a Vista 6000 gas chromatograph and a Vista 401 minicomputer control and data station. The 401 stores chromatographic methods, controls the 6000, plots chromatograms, stores chromatographic data on floppy disk, and performs recalculations on raw chromatographic data. A Valco, Inc. valve injection and switching system has been added to the 6000. This system provides for an injection of a 1 $\mu$l sample at experimental temperature and pressure (up to 5000 psi) and for sample analysis of air components plus hydrocarbons up to $C_{34}+$. A schematic of the valve system is presented in FIG. 6. All valves are air actuated by electronic relays and are thus controlled by the 401. Each valve has two positions, each of which connects adjacent valve ports. Since there are five valves, there are a total of thirty-two possible system configurations.

A typical analysis of a reservoir fluid with dissolved light components would proceed as follows. Upon command from the 401, Valve 1 switches to the inject position. The sample is carried into the column oven which is at subambient temperature so that all components heavier than butanes stay at the front end of the OV101 column ($C_1$). Air components are directed through valves 3 and 4 through a DC200/500 column ($C_2$) and through valve 5 and a molecular sieve column ($C_3$) for separation and ultimate detection on a thermal conductivity detector (TCD). The column oven then begins to heat, which drives components up through heptane through the DC200/500 column and through valve 5 to the TCD, bypassing the molecular sieve column. As the components heavier than $C_7$ begin to elute through the OV101 column, Valve 3 switches so that the sample stream is directed to the flame ionization detector (FID) for a simulated distillation analysis. Once the oven has reached a temperature of 350° C., the flow through the OV101 column is reversed so that the $C_{34}+$ components can be backflushed off the column to be detected as a group by the FID.

It should be noted that the entire series of events in the analysis is controlled from the 401 and all data recorded by the 401. It should also be noted that the heated valve enclosures, HVE-1 and HVE-2 have independent Valco ITC-K10 thermocouple controllers and may be maintained at any temperature up to 350° C. for HVE-1 and 150° C. for HVE-2.

On systems of less complexity than a reservoir crude, the sequence of chromatographic events (columns, conditions, valve switching times) can be modified as necessary.

The use of carbon dioxide in enhanced oil recovery has caused an increased interest in the fluid property behavior of carbon dioxide/hydrocarbon mixtures. Phase compositions, densities, viscosities and interfacial tensions of carbon dioxide/hydrocarbon mixtures must be known for accurate simulation of carbon dioxide displacement processes. The development of methods for predicting fluid properties of these mixtures depends on the availability of good experimental data. Although phase behavior of carbon dioxide/hydrocarbon binary mixtures have been widely reported, densities and viscosities of these fluids have generally not been measured.

Following are measurements of densities and viscosities of carbon dioxide/n-decane mixtures above their bubble point pressures. Temperatures range from 310° K. to 403° K. and pressures range from 7 MPa to 35 MPa.

Nitrogen and carbon dioxide were obtained from Welder's Supply and have nominal purities of 99.995 percent and 99.999 percent, respectively. Water was triple distilled and was degassed prior to use. N-decane was Phillips Petroleum 99.1 mole percent nominal purity and was degassed prior to use.

Specific mixture concentrations of n-decane and carbon dioxide were introduced into the apparatus of FIG. 1 by measuring specified volumes of the components from supply vessels 30 and 31. The density of n-decane was measured at the conditions of the supply vessel in the densimeter described below. The density of carbon dioxide at its supply conditions was calculated using the IUPAC carbon dioxide equation of state discussed hereinabove.

Complete mixing of the two components was achieved by flowing the fluid rapidly back and forth between vessels 20 and 21 while simultaneously stirring the fluid remaining in vessel 20 with a magnetic rotator shown in FIGS. 4 and 5.

A set of three Type E thermocouples, nickel-chromium alloy versus copper-nickel alloy (chromel-constantan), were used for temperature measurement. The thermocouples were calibrated as discussed hereinabove. One thermocouple was inserted into the densimeter 82 thermocouple well, as described below. A second thermocouple was attached to vessel 20, and the third thermocouple was attached to the capillary tube viscometer 83.

Absolute pressures were measured with a Heise gauge calibrated to 0.1 percent accuracy against a Chandler Engineering dead weight tester. Absolute pressures were also monitored at vessels 20 and 21 by calibrated Sensotec Model A-205 pressure transducers.

Differential pressures across the capillary viscometer were measured using a Sensotec Model A-5 wet/wet differential pressure transducer 89, which has a line pressure rating of 34.5 MPa. The transducer 89 was calibrated against the dead weight gauge at static conditions to $\pm 0.3$ kPa accuracy between 0 and 345 kPa differential pressure. Transducer output is read on a Sensotec Model SA-100 multifunction digital indicator which outputs a voltage signal that is recorded on a pen chart recorder. Under flowing conditions, the average of the combined repeatability and precision of the pressure reading on the differential transducer is estimated as 0.9 kPa.

Densities of n-decane and carbon dioxide were measured as discussed hereinabove and compared with literature values. The densities of carbon dioxide were measured at four pressures between 7 MPa and 34.5 MPa at each of five temperatures between 273° K. and 310° K. The average absolute deviation of the measured densities and densities calculated from the IUPAC equation of state was 1.4 kg/m$^3$ which compares to the average uncertainty of the IUPAC predictions themselves with respect to experimental data of 1.5 kg/m$^3$. Densities of n-decane were also measured at two temperatures. These results appear in Table 8 in which the measured densities from this work are compared with those of Sage, B. H.; Lavender, H. M.; Lacey, W. N., *Ind. Eng. Chem.*, 1940, 32, 743, who measured densities of a decane sample which contained some decane isomers.

The viscometer 83 consists of a stainless steel capillary tube 91 and the Sensotec differential pressure transducer 89. The tube is 731.25 cm long and has a diameter of 0.03269 ±0.00006 cm. The tube diameter was determined by measuring the pressure drop obtained when flowing n-decane through the tube at an inlet pressure of 6.89 MPa and 20.68 MPa at 310.94° K. The experimental data of Carmichael, L. T.;

Berry, Virginia M.; Sage, B. H., *J. Chem. Eng. Data*, 1969, 14, 27, were used along with the measured pressure drop and known flow rate in the Hagen-Pouiselle equation to determine the tube diameter. Carmichael et al report an uncertainty of $5.8 \times 10^{-6}$ Pa.s used for these calibrations. Experimental flow rates ranged from 16 cm³/hr to 64 cm³/hr for which the system exhibited laminar flow. Reynold's numbers were less than 0.03 and the calculated end effects for the tube were less than $10^{-9}$ Pa.s. The measured pressure differences across the tube for experimental viscosity determinations ranged from 29 kPa to 310 kPa. Accounting for the uncertainty in the tube calibration arising from Carmichael's data and the uncertainty in transducer pressure difference measurement, the uncertainty estimated for viscosity determinations is 2 percent.

Tables 9 through 13 present the density and viscosity data for carbon dioxide/n-decane mixtures for concentrations of 0.85 mole fraction n-decane to 0.15 mole fraction n-decane. All data were obtained above the mixture bubble point pressures. The estimated uncertainties in the densities is 0.5 kg/m³ and in viscosities is 2 percent. The density uncertainty increases from approximately 0.07 percent of the density for 0.85 mole fraction n-decane to approximately 0.09 percent for 0.15 mole fraction n-decane.

TABLE 1

Test of Circulating Air Bath for Temperature Homogenity

| Location of Thermocouple* | Temperature, °C. |
|---|---|
| Run No. 1 | |
| left center rear | 93.46 |
| left center front | 93.47 |
| right center rear | 93.22 |
| right center front | 93.12 |
| Run No. 2 | |
| left upper rear | 93.45 |
| left upper front | 93.56 |
| right upper rear | 93.21 |
| right upper front | 93.24 |
| Run No. 3 | |
| left upper rear | 37.12 |
| left upper front | 37.17 |
| right upper rear | 37.17 |
| right upper front | 37.19 |

*Thermocouple in air

TABLE 2

Polynomial Coefficients for Difference in Thermocouple EMF from NBS Valve versus Measured Value

| Thermocouple | $C_1^1$ (microvolts) | $C_2^1$ | $C_3^1$ | largest deviation[2] (microvolts) | standard deviation (microvolts) |
|---|---|---|---|---|---|
| 1 and 2 | −12.9614328 | 12.4547953 | 0.4485417 | 2.1 | 0.7 |
| 3 | −6.6808326 | 9.8077902 | −0.2545031 | 1.8 | 0.5 |
| 4 | −11.9715783 | 12.687928 | −0.44944996 | 2.1 | 0.6 |
| 5 | −9.7919449 | 13.2591650 | −0.4864492 | 1.0 | 0.4 |
| 6 | −9.2164427 | 12.6279584 | −0.44120111 | 1.4 | 0.4 |
| 1-1 | −16.4064369 | 14.38506 | −0.556950 | 1.5 | 0.5 |
| 2-1 | −14.9186709 | 13.68259 | −0.5095493 | 1.5 | 0.6 |
| 3-1 | −9.18147006 | 13.06657 | −0.4695258 | 2.1 | 0.7 |
| 4-1 | −9.8873441 | 13.271663 | −0.4657947 | 2.1 | 0.9 |
| 5-1 | −15.4544028 | 15.599025 | −0.6946552 | 3.8 | 0.6 |
| 6-1 | −13.7192699 | 13.868623 | −0.5525298 | 3.2 | 1.1 |

[1] $\Delta$EMF (microvolts) $= C_1 + C_2 \cdot$ EMF $+ C_3 \cdot$ EMF$^2$ where EMF is the potential drop across the thermocouple in millivolts and $\Delta$EMF is the difference between the measured potential and the standard value for a Type E thermocouple at the temperature.
[2] Largest absolute deviation between experimental values and correlated values at the same potential drop.
[3] Standard deviation of the differences between experimental and correlated values.

TABLE 3

Pressure Transducer Calibrations

| P, psig | Transducer Number | | | |
|---|---|---|---|---|
| | 1 | 2 | 3 | 4 |
| | Hysteresis[1], psi | | | |
| 1000 | 7 | 6 | 6 | 6 |
| 1000 | 6 | 4 | 4 | 4 |
| 5000 | 5 | 5 | 6 | 6 |
| 5000 | 5 | 5 | 6 | 6 |
| | Reapeatability[2], psi | | | |
| 1000 | 7 | 9 | 9 | 8 |
| 3000 | 6 | 9 | 12 | 6 |
| 5000 | 8 | 10 | 10 | 10 |
| | Accuracy[3], psi | | | |
| 1000 | −7 | −10 | −15 | −10 |
| 3000 | −16 | −20 | −25 | −21 |
| 5000 | −16 | −20 | −28 | −22 |

[1] | pressure reading (increasing pressure) - pressure reading (decreasing pressure)|
[2] | pressure reading (7/81) - pressure reading (1/82) |
[3] (Pressure reading - true absolute pressure)

TABLE 4

Correlation for k-Factors for DMA 512 Density Cells $k = A + BP$ where P is the pressure in psia, k is the instrument k-factor in g/cm³ · sec²,
$A = C_1 + C_2 t + C_3 t^2$,
$B = C_4 + C_5 t + C_6 t^2 + C_7 t^3$,
and t is temperature in degrees Celcius.

| Coefficient | Cell 1 | Cell 2 |
|---|---|---|
| $C_1$ | 3.87629453E7 | 4.23300898E7 |
| $C_2$ | −1.7835325E4 | −1.9455729E4 |
| $C_3$ | 0.0 | 9.5067556E0 |
| $C_4$ | −1.18052777E1 | −1.94405619E1 |
| $C_5$ | −0.92582134E0 | −0.38847545E0 |
| $C_6$ | 0.01572307E0 | 0.0071089E0 |

TABLE 4-continued

Correlation for k-Factors for DMA 512 Density Cells

| | | |
|---|---|---|
| $C_7$ | −7.679E-5 | −3.2731E-5 |

TABLE 5

Percentage Deviations* Between Experimental and Correlated Correlated k-Factors and Oscillation Periods for DMA512 Cells

| Temperature, °C. | Maximum k-Factor | | Average k-Factor | | Squared Oscillation Period for Water | |
|---|---|---|---|---|---|---|
| | Percent Cell 1 | Deviation Cell 2 | Percent Cell 1 | Deviation Cell 2 | Percent Cell 1 | Deviation Cell 2 |
| 32.34 | 0.02 | 0.03 | 0.006 | 0.009 | 0.0015 | 0.003 |
| 48.89 | 0.03 | 0.04 | 0.017 | 0.018 | 0.0009 | 0.007 |
| 74.45 | 0.03 | 0.10 | 0.026 | 0.081 | 0.003 | 0.020 |
| 83.75 | 0.15 | 0.20 | 0.126 | 0.194 | 0.008 | 0.020 |
| 98.18 | 0.16 | 0.17 | 0.070 | 0.141 | 0.005 | 0.020 |
| 114.96 | 0.06 | 0.08 | 0.031 | 0.025 | 0.004 | 0.005 |

*Percent Deviation = | X measured − X correlation | / X measured · 100

TABLE 6

Correlation for Oscillation Periods of Water $T^2 = A + BP$ where T is the oscillation period of water,
P is the pressure in psia,
$A = (d_1 + d_2 t + d_3 t^2) \cdot 10^{-7}$,
$B = (d_4 + d_5 t + d_6 t^2) \cdot 10^{-13}$,
and t is temperature in degrees Celcius

| Coefficient | Cell 1 | Cell 2 |
|---|---|---|
| $d_1$ | 1.473257C8E0 | 1.36087475 |
| $d_2$ | 5.53122E-4 | 5.00089E-4 |
| $d_3$ | −5.041434E-7 | −4.53535E-7 |
| $d_4$ | 1.12011355E0 | 1.0019486E0 |
| $d_5$ | −1.136089E-3 | −1.02785E-3 |
| $d_6$ | 1.457E-5 | 1.4316E-4 |

TABLE 7

Carbon Dioxide Density Measured by DMA512 vs. Density Calculated by IUPAC Equation of State

| T,°F. | P, psig | $\rho CO_2$[1] (g/cm³) | Tolerance of $\rho CO_2$ %[2] | $\Delta \rho$ (g/cm³)[3] | Percent Difference in $\rho CO_2$ and $\rho$ expt[4] |
|---|---|---|---|---|---|
| 32.00 | 1000 | 0.2419 | 0.5 | 0.0015 | 0.60 |
| | 1500 | 0.7616 | 0.5 | 0.0002 | 0.03 |
| | 3000 | 0.8870 | 0.1 | 0.0008 | 0.09 |
| | 4000 | 0.9293 | 0.1 | 0.0011 | 0.12 |
| | 5000 | 0.9615 | 0.1 | 0.0016 | 0.17 |
| 48.57 | 1500 | 0.4703 | 0.5 | −0.0017 | 0.36 |
| | 3000 | 0.8023 | 0.3 | −0.0011 | 0.14 |
| | 4000 | 0.8617 | 0.2 | −0.0003 | 0.03 |
| | 5000 | 0.9029 | 0.1 | 0.0005 | 0.06 |
| 65.10 | 1500 | 0.2884 | 0.3 | −0.0045 | 1.56 |
| | 3000 | 0.7055 | 0.2 | −0.0030 | 0.43 |
| | 4000 | 0.7893 | 0.1 | −0.0017 | 0.22 |
| | 5000 | 0.8422 | 0.1 | −0.0006 | 0.07 |
| 81.64 | 1500 | 0.2330 | 0.4 | −0.0017 | 0.73 |
| | 3000 | 0.6029 | 0.2 | −0.0007 | 0.12 |
| | 4000 | 0.7138 | 0.2 | −0.0006 | 0.08 |
| | 5000 | 0.7801 | 0.1 | −0.0002 | 0.03 |
| 98.18 | 1500 | 0.2027 | 0.4 | −0.0013 | 0.64 |
| | 3000 | 0.5102 | 0.3 | −0.0032 | 0.63 |
| | 4000 | 0.6394 | 0.1 | −0.0020 | 0.41 |
| | 5000 | 0.7186 | 0.1 | −0.0009 | 0.13 |

[1] Density of carbon dioxide from Reference 2.
[2] Tolerance of carbon dioxide density for the IUPAC formulation as compared with all reported experimental data.
[3] Difference in carbon dioxide density from S. Angus, et al, ed., "International Thermodynamic Tables of the Fluid State - Carbon Dioxide," Pergamon Press, 1976, and that measured on DMA512 cell 1.
[4] Percent difference in carbon dioxide density from Angus et al and DMA 512 cell 1.

TABLE 8

DENSITIES OF DECANE

T = 310.94 K

| | Density (kg/m³) | |
|---|---|---|
| | 7.10 MPa | 20.64 MPa |
| This work (n-decane) | 723.2 | 733.7 |
| Sage (decane)[a] | 725.8 ± 1.5 | 737.6 ± 1.5 |
| Sage (corrected)[b] | 721.5 | 733.2 |
| TRAPP[3] | 725.3 | 733.8 |

T = 303.56 K

| | Density (kg/m³) | |
|---|---|---|
| | 6.89 MPa | 13.79 MPa |
| This work | 728. | 733. |
| TRAPP[c] | 731. | 736. |
| COSTALD[d,e] | 728. | 733. |

[a] Sage, B. H.; Lavender, H. M.; Lacey, W. N., Ind. Eng. Chem 1940, 32, 743.
[b] Measured density for decane sample reduced by 0.6 percent for the difference between decane and n-decane, as measured by Shepard, A. F.; Henne, A. L.; Midgley, Jr. T., J. Am. Chem Soc. 1931, 53, 1948.
[c] Ely, James F.; Hanley, H. J. M., Proceedings of Sixtieth Annual Convention, Gas Processors Assoc., San Antonio, TX, March 23-25, 1981.
[d] A correction for pressure has been added to the denesity at saturation pressure obtained from COSTALD.
[e] Hankinson, Risdon W.; Thomson, George H., AIChE J 1979, 25, 653.

TABLE 9

DENSITY AND VISCOSITY OF BINARY MIXTURE OF N—DECANE (0.850 MOLE FRACTION) AND CARBON DIOXIDE (0.150 MOLE FRACTION)

| Pressure MPa | Temperature K. | Density kg/m³ | Temperature K. | Viscosity $10^{-6}$ Pa · s |
|---|---|---|---|---|
| 6.93 | 310.93 | 728.1 | 310.91 | 666.6 |
| 14.06 | | 734.1 | | 704.5 |
| 20.81 | | 739.9 | | 752.7 |
| 28.37 | | 745.0 | | 812.3 |
| 34.63 | | 749.3 | | 864.7 |
| 6.72 | 344.32 | 701.5 | 344.33 | 446.2 |
| 14.17 | | 709.5 | | 484.1 |
| 20.89 | | 716.1 | | 516.6 |
| 27.89 | | 722.1 | | 558.8 |
| 34.58 | | 726.9 | | 587.7 |
| 7.10 | 373.13 | 678.3 | 373.15 | 333.6 |
| 13.96 | | 687.4 | | 371.5 |
| 21.06 | | 694.9 | | 399.8 |
| 27.75 | | 702.3 | | 432.3 |
| 34.68 | | 708.1 | | 464.6 |
| 7.19 | 403.08 | 652.4 | 403.22 | 269.5 |
| 14.48 | | 665.6 | | 292.3 |
| 21.30 | | 675.6 | | 318.2 |
| 27.96 | | 683.7 | | 342.6 |
| 34.06 | | 690.4 | | 363.7 |

TABLE 10

DENSITY AND VISCOSITY OF BINARY MIXTURE OF N—DECANE (0.699 MOLE FRACTION) AND CARBON DIOXIDE (0.301 MOLE FRACTION)

| Pressure MPa | Temperature K. | Density kg/m³ | Temperature K. | Viscosity $10^{-6}$ Pa · s |
|---|---|---|---|---|
| 7.16 | 310.92 | 735.1 | 310.90 | 547.1 |
| 14.28 | | 740.9 | | 589.2 |
| 21.06 | | 746.9 | | 629.8 |
| 27.72 | | 752.9 | | 669.9 |
| 34.09 | | 757.8 | | 709.9 |
| 7.02 | 344.31 | 704.4 | 344.31 | 388.7 |
| 14.13 | | 712.7 | | 413.7 |
| 20.86 | | 720.2 | | 442.9 |
| 27.83 | | 727.4 | | 476.3 |
| 34.51 | | 733.1 | | 506.1 |
| 6.76 | 374.01 | 676.7 | 374.02 | 288.1 |
| 13.72 | | 687.5 | | 309.5 |
| 20.99 | | 697.4 | | 339.3 |
| 27.75 | | 705.1 | | 366.1 |
| 33.96 | | 711.9 | | 390.5 |
| 7.10 | 403.08 | 650.8 | 403.22 | 225.8 |
| 14.24 | | 664.4 | | 246.0 |
| 20.86 | | 675.8 | | 271.3 |

TABLE 10-continued

DENSITY AND VISCOSITY OF
BINARY MIXTURE OF N—DECANE (0.699 MOLE FRACTION) AND CARBON DIOXIDE (0.301 MOLE FRACTION)

| Pressure MPa | Temperature K. | Density kg/m³ | Temperature K. | Viscosity $10^{-6}$ Pa·s |
|---|---|---|---|---|
| 27.78 | | 685.6 | | 291.4 |
| 33.89 | | 693.3 | | 308.6 |

TABLE 11

DENSITY AND VISCOSITY OF BINARY
MIXTURE OF N—DECANE (0.495 MOLE FRACTION) AND
CARBON DIOXIDE (0.505 MOLE FRACTION)

| Pressure MPa | Temperature K. | Density kg/m³ | Temperature K. | Viscosity $10^{-6}$ Pa·s |
|---|---|---|---|---|
| 7.12 | 311.25 | 750.5 | 311.21 | 360.1 |
| 13.87 | | 758.9 | | 393.5 |
| 20.61 | | 766.9 | | 420.0 |
| 27.65 | | 774.6 | | 447.7 |
| 30.94 | | 778.0 | | 464.0 |
| 6.93 | 343.14 | 712.9 | 343.18 | 289.3 |
| 13.63 | | 724.7 | | 286.6 |
| 20.54 | | 735.4 | | 325.5 |
| 27.58 | | 744.6 | | 333.6 |
| 10.60 | 373.20 | 685.4 | 373.36 | 212.9 |
| 13.82 | | 692.7 | | 222.2 |
| 20.23 | | 705.2 | | 243.0 |
| 27.75 | | 717.2 | | 266.1 |
| 11.58 | 402.94 | 652.8 | 403.30 | 169.2 |
| 13.91 | | 659.0 | | 174.9 |
| 21.37 | | 677.9 | | 199.0 |
| 27.99 | | 691.1 | | 215.3 |

TABLE 12

DENSITY AND VISCOSITY OF BINARY
MIXTURE OF N—DECANE (0.351 MOLE FRACTION)
AND CARBON DIOXIDE (0.649 MOLE FRACTION)

| Pressure MPa | Temperature K. | Density kg/m³ | Temperature K. | Viscosity $10^{-6}$ Pa·s |
|---|---|---|---|---|
| 7.50 | 312.46 | 760.1 | 312.42 | 266.8 |
| 13.97 | | 770.2 | | 293.2 |
| 20.61 | | 780.2 | | 306.8 |
| 27.82 | | 789.8 | | 330.0 |
| 10.44 | 345.12 | 719.0 | 345.14 | 184.6 |
| 13.95 | | 727.9 | | 192.7 |
| 20.68 | | 742.5 | | 212.3 |
| 27.72 | | 755.1 | | 229.4 |
| 12.35 | 373.52 | 681.4 | 373.67 | 155.4 |
| 14.72 | | 689.4 | | 160.2 |
| 20.72 | | 705.6 | | 177.9 |
| 27.70 | | 721.1 | | 194.2 |
| 14.11 | 402.77 | 643.2 | 403.11 | 125.5 |
| 20.94 | | 668.2 | | 147.5 |
| 27.68 | | 688.5 | | 165.6 |

TABLE 13

DENSITY AND VISCOSITY OF BINARY
MIXTURE OF N—DECANE (0.150 MOLE FRACTION)
AND CARBON DIOXIDE (0.850 MOLE FRACTION)

| Pressure MPA | Temperature K. | Density kg/m³ | Temperature K. | Viscosity $10^{-6}$ Pa·s |
|---|---|---|---|---|
| 8.72 | 312.46 | 774.4 | 312.41 | 138.8 |
| 13.68 | | 795.8 | | 148.4 |
| 20.65 | | 818.1 | | 161.1 |
| 27.75 | | 836.8 | | 174.6 |
| 13.30 | 345.12 | 695.7 | 345.17 | 98.2 |
| 20.54 | | 745.4 | | 118.0 |
| 27.76 | | 775.1 | | 133.7 |
| 17.20 | 373.70 | 641.3 | 373.85 | 95.7 |
| 22.06 | | 682.5 | | 106.3 |
| 28.03 | | 716.7 | | 118.3 |
| 19.23 | 402.80 | 571.6 | 403.14 | 93.7 |
| 23.30 | | 618.8 | | 105.5 |

TABLE 13-continued

DENSITY AND VISCOSITY OF BINARY
MIXTURE OF N—DECANE (0.150 MOLE FRACTION)
AND CARBON DIOXIDE (0.850 MOLE FRACTION)

| Pressure MPA | Temperature K. | Density kg/m³ | Temperature K. | Viscosity $10^{-6}$ Pa·s |
|---|---|---|---|---|
| 27.54 | | 651.4 | | 116.0 |

What is claimed is:

1. A system for measuring properties of fluids comprising:
a pair of high pressure cells, each one of said cells including a floating piston therein separating each of said cells into a fluid analysis chamber and a hydraulic fluid chamber,
means for selectively controlling the amount of pressure applied to said hydraulic fluid chamber of each cell whereby the pressure of the fluid in said fluid analysis chamber is defined, and
means interconnecting said fluid analysis chamber of each of said cells for passing fluid to be analyzed between each of said cells.

2. The system of claim 1 wherein at least one of said cells has a bar magnet in the fluid analysis chamber, and wherein means are provided externally of said cell for agitating said bar magnet.

3. The system of claim 1 wherein each one of said cells has a bar magnet in the fluid analysis chamber, and wherein means are provided externally of said cells for agitating said bar magnet.

4. The system of claim 2 wherein said means for passing fluids between said cells includes a densimeter and a viscometer.

5. The system of claim 1 wherein properties of fluids used in enhanced oil recovery are measured.

6. The system of claim 5 wherein, one of said fluids is carbon dioxide and wherein another of said fluids is a hydrocarbon.

7. The system of claim 5 wherein said properties measured by said system include phase equilibria, phase volumes, compositions, densities, viscosities, and interfacial tensions of fluids.

8. The system of claim 1 further comprising a chromatograph system.

9. A method of measuring properties of fluids with a pair of high pressure cells, each one of said cells including a floating piston therein separating each of said cells into a fluid analysis chamber and a hydraulic fluid chamber, comprising the steps of:
passing fluid for analysis between each of said fluid analysis chambers, and
concurrently agitating at least one of said cells by magnetic means.

10. The method of claim 9 wherein both of said cells are agitated by magnetic means while fluid for analysis is being passed between said fluid analysis chambers.

11. The method of claim 9 wherein said passing of fluid between said fluid analysis chambers further comprises measuring properties of said fluid.

12. The method of claim 9 wherein said cell has a length and said magnetic agitation comprises applying substantially continuous magnetic agitation force the entire length of said fluid analysis chamber whereby said magnetic agitation occurs at essentially all positions along said length.

13. The system of claim 2 wherein said at least one high pressure cell containing said bar magnet is in the vertical position with said fluid analysis chamber arranged on top whereby said bar magnet rests on said floating piston.

14. The system of claim 13 wherein said external agitating means comprises a cylinder bearing a substantially continuous magnetic field the length thereof and mounted for rotation around said at least one high pressure cell whereby said bar magnet is agitated upon rotation of said cylinder at all positions along the length of said at least one high pressure cell.

15. The system of claim 14 wherein said substantially continuous magnetic field is provided by a series of magnet pairs arranged along the length of said cylinder at a position about 180° from each other.

16. The system of claim 15 wherein there are at least seven said pairs of magnets which are discs.

* * * * *

UNITED STATES PATENT AND TRADEMARK OFFICE
CERTIFICATE OF CORRECTION

PATENT NO. : 4,530,234

DATED : July 23, 1985

INVENTOR(S) : CULLICK et al.

It is certified that error appears in the above-identified patent and that said Letters Patent is hereby corrected as shown below:

Column 14, Table 2 under "$C_1$" (last line)     "-13.7192699" should be -- -13.71924699 --

Column 15, Table 7 under $\Delta p$ $(g/cm^3)^3$ (second to last line)     "-0.0020" should be -- -0.0026 --.

Signed and Sealed this

Fifteenth Day of October 1985

[SEAL]

Attest:

Attesting Officer

DONALD J. QUIGG

Commissioner of Patents and Trademarks—Designate